US011285089B2

(12) United States Patent
Balke et al.

(10) Patent No.: US 11,285,089 B2
(45) Date of Patent: Mar. 29, 2022

(54) BLEACHING COMPOSITION

(71) Applicant: KAO GERMANY GMBH, Darmstadt (DE)

(72) Inventors: Axel Balke, Darmstadt (DE); Diane Bauer, Darmstadt (DE); Clarissa Lipinski, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 17/076,301

(22) Filed: Oct. 21, 2020

(65) Prior Publication Data
US 2021/0128429 A1 May 6, 2021

(30) Foreign Application Priority Data

Oct. 31, 2019 (EP) .................. 19206635

(51) Int. Cl.
| | |
|---|---|
| *A61Q 5/08* | (2006.01) |
| *A61K 8/25* | (2006.01) |
| *A61K 8/02* | (2006.01) |
| *A61K 8/04* | (2006.01) |
| *A61K 8/23* | (2006.01) |
| *A61K 8/362* | (2006.01) |
| *A61Q 5/10* | (2006.01) |

(52) U.S. Cl.
CPC ............... *A61K 8/25* (2013.01); *A61K 8/022* (2013.01); *A61K 8/044* (2013.01); *A61K 8/23* (2013.01); *A61K 8/362* (2013.01); *A61Q 5/08* (2013.01); *A61Q 5/10* (2013.01); *A61K 2800/432* (2013.01); *A61K 2800/48* (2013.01); *A61K 2800/51* (2013.01); *A61K 2800/5426* (2013.01)

(58) Field of Classification Search
CPC ...... A61K 8/22; A61K 2800/31; A61K 8/362; A61K 8/022; A61K 2800/48; A61K 2800/432; A61K 8/25; A61K 2800/51; A61K 2800/5426
USPC .......................................................... 424/62
See application file for complete search history.

(56) References Cited

U.S. PATENT DOCUMENTS

| | | | |
|---|---|---|---|
| 5,888,484 A | 3/1999 | Schmitt et al. | |
| 5,989,530 A | 11/1999 | Lorenz et al. | |
| 7,220,285 B2 | 5/2007 | Legrand et al. | |
| 2006/0236469 A1* | 10/2006 | Bone ................. | A61Q 5/04 8/405 |
| 2006/0242771 A1* | 11/2006 | Bone ................. | A61Q 5/065 8/405 |
| 2009/0095315 A1* | 4/2009 | De La Mettrie .... | A61K 8/22 132/208 |
| 2013/0022565 A1* | 1/2013 | Braida-ValeRio ... | A61K 8/22 424/62 |
| 2017/0007856 A1* | 1/2017 | Aubert ............... | A45D 37/00 |
| 2017/0290749 A1 | 10/2017 | Borgnini et al. | |
| 2017/0340553 A1 | 11/2017 | Anderheggen et al. | |

FOREIGN PATENT DOCUMENTS

| | | |
|---|---|---|
| DE | 10 2016 209464 A1 | 11/2017 |
| EP | 560 088 B1 | 9/1993 |
| EP | 778 020 A1 | 6/1997 |
| JP | 2006-225354 A | 8/2006 |

OTHER PUBLICATIONS

European Search Report dated May 6, 2020, issued in connection with European Patent Application No. 19206635.5.

\* cited by examiner

*Primary Examiner* — Eisa B Elhilo

(74) *Attorney, Agent, or Firm* — Norris McLaughlin, P.A.

(57) ABSTRACT

The present invention relates to a bleaching composition for keratin fibres, especially human hair, comprising at least one compound with bleaching effect and two different silicate based alkalizing agents.

15 Claims, No Drawings

BLEACHING COMPOSITION

This application claims foreign priority benefits under 35 U.S.C. § 111 of European Application No. 19206635.5, filed Oct. 31, 2019, the disclosure of which is incorporated herein by reference.

The present invention relates to a bleaching composition for keratin fibres, especially human hair, comprising at least one compound with bleaching effect and two different silicate based alkalizing agents.

Hair bleaching is a common practice for ages. It is based on oxidative decomposition of hair colour, which is usually done using peroxide or peroxide releasing compounds such as persulfates. Due to highly irritating potential of these bleaching ingredients and dustiness of powder compositions, it is preferred to provide granular composition where dust is reduced by agglomerating small particles into granulates using various binding agents. Most popular binding agent is mineral oil, which was the subject matter of EP 560 088 B1. Furthermore, EP 778 020 A1 suggests the use of oil and wax compounds or their mixtures for preparation of suspensions.

The bleaching of human hair customarily consists of a process with the following steps: Homogenous mixing of a water-free preparation, preferably a powder, comprising at least one compound with a bleaching effect, in particular a solid peroxide salt, preferably ammonium, potassium and/or sodium persulfate or earth alkali peroxide and an alkalizing agent, with an aqueous hydrogen peroxide composition, application of this composition onto the hair, and rinsing off the hair after bleaching is completed. It has been known for some time that use of these compositions is effective with regard to the bleaching, but it can lead to hair damage and/or scalp irritation, especially due to the use of highly alkaline compositions. Especially hair damaging problems are aggravated with repeatedly bleaching hair. Therefore, it is important that consumers are provided with effective bleaching compositions with less damaging side effects on hair and scalp. Unfortunately, due to the strong oxidative activity and alkalinity some level of damage must be accepted.

The damaged hair is often difficult to handle cosmetically, looks brittle, loses its elasticity and especially does not appear attractive. There is a high demand of reducing hair damage so that the hair may be treated subsequently with various hair preparations such as shampoos, conditioners, styling compositions etc., to obtain cosmetically acceptable appearance and manageable hair.

Therefore, aim of the present invention is to find out a composition for bleaching hair especially human hair which does effectively beach hair but causes less damage so that repeated bleaching processes may be done without causing excessive damage to hair.

The inventors of the present invention have surprisingly found out that a bleaching composition based at least one compound with bleaching effect and furthermore comprising two different alkalizing agents wherein the one is a metasilicate salt and the other being a disilicate salt at a specific weight ratio range bleaches hair effectively and causes less damage to the hair.

Accordingly, the first object of the present invention is a substantially water free bleaching composition for keratin fibres, especially human hair, comprising one or more persalts, one or more metasilicate salts and one or more disilicate salts wherein the total concentration by weight of one or more metasilicate salts is higher than the total concentration by weight of one or more disilicate salts.

U.S. Pat. No. 7,220,285 discloses bleach powder compositions comprising sodium metasilicate and sodium disilicate. In the compositions sodium disilicate concentration is higher than sodium metasilicate concentration, so that the disclosure is completely opposite to the findings of the present invention.

The second object of the present invention is the use of the substantially water free composition for effectively bleaching keratin fibres, especially human hair.

With the term "substantially water-free bleaching composition" it is meant that no additional water is introduced into the composition other than bound water which may be as high as 1%, by weight, of the composition.

The third object of the present invention is a process for bleaching hair wherein the composition of the present invention is mixed with an aqueous composition comprising one or more oxidizing agents, preferably hydrogen peroxide, and having a pH in the range of 1 to 5 and thus obtained composition is applied onto hair and left on the hair for a period of 5 to 45 min and rinsed off from hair.

The fourth object of the present invention is a kit for hair comprising a composition of the present invention and an aqueous composition comprising one or more oxidizing agents, preferably hydrogen peroxide and having a pH in the range of 1 to 5.

The composition comprises one or more compounds with bleaching effect. Suitable compounds are in general peroxides. Useful as such are in particular persulfates such as sodium, potassium and ammonium persulfate, earth alkali peroxides such as magnesium peroxide, melamine peroxide or urea peroxide or phtholimidoperoxyhexanoic acid, and mixtures thereof. The total concentration of these compounds is at least 5%, preferably in the range of 15 to 80%, more preferably 20 to 60% and most preferably 25 to 55% by weight, calculated to the total composition.

The concentrations and concentration ranges given throughout this specification are all calculated to the total composition prior to mixing with an aqueous composition comprising one or more oxidizing agent and having a pH in the range of 1 to 5, unless otherwise stated.

The composition comprises one or more metasilicate salts. The suitable non-limiting examples are sodium metasilicate, potassium metasilicate, and ammonium metasilicate. The preferred metasilicate salt is sodium metasilicate.

The composition comprises one or more disilicate salts. The suitable non-limiting examples are sodium, potassium and ammonium disilicates. The preferred is sodium disilicate.

The total concentration of the metasilicate salts and the disilicate salts is in the range of 2 to 30%, preferably 3 to 25% and more preferably 5 to 20% by weight, calculated to the total composition. The weight ratio of metasilicate salts to disilicate salts is in the range of 10:1 to 1.1:1, preferably 8:1 to 2:1.5, more preferably 5:1 to 3:1.5 and most preferably it is 2:1.

In a preferred form of the present invention, the composition comprises one or more ammonium salts which is different from persalts/peroxides and metasilicate and disilicate salts. The total concentration of one or more ammonium salts is in the range of 0.1% to 10% by weight, calculated to total composition. Suitable ammonium salts are ammonium carbonate, ammonium hydrogen carbonate, ammonium carbamate, ammonium chloride, ammonium sulfate, ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate. Compositions may also comprise mixture or ammonium salts.

Preferred thereof are the ammonium phosphates, such as ammonium dihydrogen phosphate, ammonium hydrogen phosphate, diammonium sodium phosphate, sodium ammonium hydrogen phospahe, ammonium disodium phosphate, as well as ammonium chloride, ammonium sulphate, diammonium hydrogen citrate, ammonium carbonate and ammonium hydrogen carbonate.

In addition to the active compounds, substantially water free bleaching compositions also comprise inert pulverulent carrier materials such as silicium dioxide, starch powder, diatomaceous earth and kaolin. Particularly preferred inert carrier material is kaolin as it improves the cosmetic appearance of the ready to use composition, after mixing with the aqueous oxidizing composition. The composition comprising kaolin produces more creamy appearing compositions with appropriate consistency.

The substantially water free bleaching composition may be in the form of powder, suspension and paste. In a preferred embodiment of the present invention, substantially water free bleaching composition is in powder form and in particular in a dust free powder form and, therefore, comprises oily lipophilic compounds such as vegetable oils, for example, jojoba oil or any other; petrolatum liquid paraffins, especially paraffinum perliquidum and parafiinum subliquidum, silicone oils such as dimethicones with various viscosity available from Dow Corning under the trade name DC 200, arylated silicones such as phenyl methicone, phenyl trimethicone, diphenyl dimethicone, diphenylsiloxy phenyl trimethicone, tetramethyl tetraphenyl trisiloxane, triphenyl trimethicone, tetramethly tetraphenyl trisiloxane and pentaphenyl trimethyl trisiloxane; hydropobic fatty acid esters such as octyl palmitate, isocetyl palmitate, isopropyl palmitate and octyl stearate, $C_{10}$- to $C_{36}$-fatty acid triglycerides, as well as their mixtures. The preferred ones are silicone oils, jojoba oil, fatty acid esters, paraffin oils, combinations of fatty acid esters and paraffin oils. Fatty acid esters and/or paraffin oils and/or silicone oils are particularly preferred. Total concentration of these oily lipophilic compounds is in the range of 0.1 to 50% by weight, preferably 0.5 to 40%, more preferably 1 to 35% and most preferably 2.5 to 30% by weight, calculated to the total composition.

The powder composition can be produced with processes such as by mixing the powdery ingredients first and subsequently adding lipophilic ingredient(s) and by fluidized bed method. In fluidized bed method, powder ingredients are mixed in a vessel and made flowing by inletting an air flow which may be heated (preferred when using waxy component) or carried out at room (ambient) temperature and while the powder mix freely "flowing" lipophilic ingredient and/or mixture with any other liquid component is sprayed from a nozzle mounted above the powder batch.

The average particle size of the dust free bleaching powder composition according to the invention is generally range below 1 mm, preferably below 500 μm, more preferably less than 400 μm and in particular about 25 to about 100 μm, thus ensuring excellent processing capability, i.e. miscibility with an aqueous hydrogen peroxide solution prior to application onto human hair.

Further, in another preferred form of the invention substantially water free bleaching composition comprises one or more thickening polymers. Suitable ones are cellulose, alginate, polysaccharides and acrylic acid polymers. One or more thickening polymers is(are) preferably selected from methyl cellulose, ethyl cellulose, hydroxyethylcellulose, methylhydroxyethylcellulose, methylhydroxypropylcellulose, carboxymethyl cellulose, alginic acid and its sodium and ammonium salts, gum arabic, guar gum, xanthan gum, and acrylic acid polymers with molecular weights from about 1,250,000 to 4,000,000, and their mixtures. The polymers are used in a total concentration in the range of 0.1 to 15%, preferably 0.2 to 10%, and more preferably 0.5 to 7.5% and in particular 0.5 to 5% by weight, calculated to total composition.

In another preferred form of the present invention, substantially water free bleaching composition comprise cationic polymers primarily as conditioning agents which may also have a thickening effect. Suitable are cationic cellulose polymers know as Polymer JR type from Amerchol such as Polyquaternium 10 or cationic guar gum known with trade name Jaguar from Rhone-Poulenc and chemically for example Guar hydroxypropyl trimonium chloride. Furthermore, chitosan and chitin can also be included in the compositions as cationic natural polymers. Further suitable cationic polymers are known from hair conditioning and styling compositions known with their CTFA category name Polyquaternium. Typical examples are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87.

The cationic polymers as conditioners are comprised at a total concentration in the range of 0.1-7.5%, preferably 0.2-5% by weight and more preferably 0.25-2.5% by weight, calculated to total composition. It should be noted that within the meaning of the present invention the concentrations given in this paragraph is specifically for the conditioning cationic polymers and not for the thickening polymers.

The composition preferably comprises one or more chelating agents at a total concentration in the range of 0.1-10%, preferably 0.2-7.5% by weight and more preferably 0.25-5% by weight, calculated to total composition. Suitable preferred examples are EDTA and its mono, di, tri and tetra monovalent cation salts and their mixtures and gluconic acid and its salts and their mixtures.

In a particularly preferred embodiment of the present invention, the composition comprises one or more dicarboxylic acids for further reducing hair damage. Suitable ones are C2 to C8 saturated or mono unsaturated ones, which may as well be substituted with one or more hydroxyl groups. Suitable non-limiting examples are malic, succinic, oxalic, malonic, glutaric adipic, pimelic, suberic, maleic, fumaric, glutaconic, tartronic and tartaric acids and their mixtures. Preferred are malic, succinic, and maleic acids. Particularly preferred one is malic acid. The dicarboxylic acids are comprised at a total concentration in the range of 0.1 to 5%, preferably 0.2 to 4%, more preferably 0.25 to 3% by weight calculated to the total composition.

The substantially water free bleaching composition can comprise one or more direct dyes. Suitable direct dyes are anionic, cationic, non-ionic nitro dyes and plant dyes.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9, Disperse Violet 1, HC Red 18, HC Blue 18 and HC Yellow 16 and their alkali metal salts such as sodium, potassium. Among those, the most preferred anionic dyestuffs are Acid Red 52, DC Violet 2, DC Red 33, DC Orange 4, DC Red 27, DC Yellow 10 HC Red 18, HC Blue 18 and HC Yellow 16.

Suitable cationic dyes are in principal those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87 and Basic Orange 31. The particularly suitable ones are Basic red 51, Basic Yellow 87 and Basic Orange 31 sold by CIBA.

Additionally, the compositions comprise neutral dyes (HC dyes), so called nitro dyes. Suitable examples are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Red No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs are also comprised either alone or in combination with synthetic direct-acting dyestuffs, for example henna (red or black), alkanna root, laccaic acid, indigo, logwood powder, madder root and rhubarb powder, etc.

One or more direct dyes are comprised at a total concentration in the range 0.1 to 15%, preferably 0.2 to 10% and more preferably 0.25 to 7.5% by weight calculated to the total composition. The composition can also comprise mixture of several direct dyes i.e. an anionic, a cationic and/or a nonionic ones. In such a case the dyes may be mixed at any ratio with each other.

The compositions of the present invention may comprise one or more magnesium and/or calcium salt in order to prevent heating up and/or foaming when mixed with an aqueous composition comprising at least one oxidizing agent. Both organic and inorganic salts are suitable for the purpose of the present invention. Inorganic salts are most preferred. Suitable magnesium salts are magnesium aluminium borosilicate, magnesium aspartate, magnesium borate, magnesium bromate, magnesium bromide, magnesium benzoate, magnesium acetate, magnesium carbonate, magnesium citrate, magnesium clorate, magnesium dihydrogen phosphate, magnesium fluoride, magnesium formate, magnesium hydroxide, magnesium iodide, magnesium lactate, magnesium mandalate, magnesium monofluorophosphate, magnesium oxalate, magnesium oxide, magnesium perborate, magnesium phosphate, magnesium propionate, magnesium pyrophosphate, magnesium salicylate, magnesium silicate, and magnesium tartarate.

Suitable calcium salts are calcium aluminium borosilicate, calcium aspartate, calcium benzoate, calcium acetate, calcium carbonate, calcium citrate, calcium dihydrogen phosphate, calcium fluoride, calcium hydroxide, calcium lactate, calcium monofluorophosphate, calcium oxide, calcium phosphate, calcium propionate, calcium pyrophosphate, calcium sulphate, calcium nitrate, calcium salicylate, calcium silicate, hydrate, calcium tartarate, tricalcium phosphate, calcium chloride, calcium iodide and calcium bromide.

The total concentration of one or more magnesium and/or calcium salt in the compositions of the present invention is between 0.1 and 20%, preferably between 0.5 and 15%, more preferably between 0.75 and 10% and most preferably between 1 and 7.5% by weight calculated to total composition.

The composition of the present invention may comprise additional substances such as surfactants, binding agents, fragrances, powder gliding agents such as colloidal silicium dioxide. In order to avoid repetition, reference is made to the respective standard literature, for example, K. Schrader and A. Domsch, "Cosmetology—Theory and Practice (2005, Verlag für Chemische Industrie), pages 142 to 151.

The bleaching and/or highlighting composition of the present invention is mixed prior to application with an oxidizing lotion comprising at least one oxidizing agent. The oxidizing agents suitable are hydrogen peroxide, urea peroxide, melamin peroxide or perborate salts. The most preferred is hydrogen peroxide. Such composition comprises 2 to 12% by weight at least one oxidizing agent preferably hydrogen peroxide and is either a solution or in the form of an emulsion. The mixing ratio is very much dependent on the level of bleaching effect targeted, i.e. the level of highlighting and/or bleaching and darkness of hair before bleaching, and can be adjusted accordingly by hair dressers. However, generally mixing ratio is within the range of 0.5 to 4 by weight (bleaching composition to oxidizing composition), preferably in the range of 1 to 2 by weight.

The pH of the ready to use product, mixture of bleaching composition and oxidizing lotion, is in the range of 8 to 12, in particular between 9 and 11.

The invention is illustrated with the following examples, but not limited to.

EXAMPLE 1

|  | Concentration % by weight | | |
| --- | --- | --- | --- |
|  | A | B | C |
| Potassium persulfate | 40 | 40 | 40 |
| Sodium persulfate | 5 | 5 | 5 |
| Ammonium carbonate | 1 | 1 | 1 |
| Sodium metasilicate | 10 | 7.5 | 15 |
| Sodium disilicate | 5 | 7.5 | — |
| Diatomaceous Earth | 39 | 39 | 39 |

The composition A is according to the present invention and the compositions B and C are comparative compositions in order to show the effect of the invention.

The above compositions were prepared by combining all powder components together and mixing until homogeneity in a suitable mixer.

The above bleaching powder compositions were mixed with the following oxidizing composition at a weight ratio of powder to oxidizing lotion 1:2.

Oxidizing Lotion

| Hydrogen peroxide | 9.00 (% by wt.) |
| --- | --- |
| Phosphoric acid | 0.50 |
| Disodium hydrogen phosphate | 0.10 |
| Salicylic acid | 0.10 |
| Water | ad 100.00 |

After obtaining a homogeneous mixture, it was applied onto hair having colour at level 6, left on the hair for 30 min at ambient temperature and rinsed off with water. The hair was shampooed once and dried with a hair drier. The colour of the streaks were measured before and after bleaching with a laboratory colorimeter of the brand Minolta. The obtained values were used to calculate the colour differences with the well-known equation in the art.

Hair damage was assessed by measuring the elasticity of individual hair fibres with stress strain technique. Therefore, 25 individual hair fibres with the length of 30 mm were wet with water and strained at a 100%/minute using MTT680 instrument (Dia-Stron Limited, Andover, UK). The force to strain hair fibre at 2% were obtained in MPa. The higher number indicates the less damage of the hair. The damage values were calculated as the reciprocal of the strain force at 2%. Afterwards, the damage per bleaching level was calculated by dividing the damage value with the DL, the intensity difference between unbleached hair and bleached hair.

Following results were obtained.

| Composition | L value | ΔL | Force at 2% (MPa) | Damage | Damage/ΔL |
| --- | --- | --- | --- | --- | --- |
| A | 40.1 | 21.02 | 47.01 | 0.021 | 0.0010 |
| B | 38.8 | 19.01 | 45.44 | 0.022 | 0.0012 |
| C | 35.7 | 15.9 | 45.92 | 0.022 | 0.0014 |

Form the above results; it is beyond any doubt that the composition A causes the lowest damage to the hair. Furthermore, the bleaching effect of the composition A is the highest as well. In other words, the composition A delivered the most intensive bleaching effect with the least damage to the hair.

EXAMPLE 2

| Hydroxyethylcellulose | 1.00% by weight |
| --- | --- |
| Cellulose gum | 3.00 |
| Tetrasodium EDTA | 2.00 |
| Ammonium carbonate | 1.00 |
| Ammonium persulfate | 21.00 |
| Potassium persulfate | 35.00 |
| Sodium metasilicate | 10.00 |
| Sodium disilicate | 5.00 |
| Diatomaceous Earth | 20.00 |
| Polyquaternium - 10 | 1.00 |
| Malic acid | 1.00 |

The hair was intensively bleached with the above composition with less hair damage.

EXAMPLE 3

| Hydroxyethylcellulose | 1.00% by weight |
| --- | --- |
| Cellulose gum | 3.00 |
| Tetrasodium EDTA | 2.00 |
| Ammonium carbonate | 1.00 |
| Ammonium persulfate | 21.00 |
| Potassium persulfate | 35.00 |
| Sodium metasilicate | 10.00 |
| Sodium disilicate | 5.00 |
| Kaolin | 10.00 |
| Paraffin oil | 10.00 |
| Polyquaternium - 10 | 1.00 |
| Malic acid | 1.00 |

The above composition is a dust free powder bleach composition showing similar bleaching effect with the previous examples.

The invention claimed is:

1. A substantially water free composition for bleaching keratin fibers, the composition comprising:
   one or more persalts;
   one or more metasilicate salts; and
   one or more disilicate salts,
   wherein a total concentration by weight of the one or more metasilicate salts is higher than a total concentration by weight of the one or more disilicate salts.

2. The composition according to claim 1 wherein the one or more persalts are selected from ammonium persulfate, sodium persulfate, and potassium persulfate.

3. The composition according to claim 1, wherein the one or more persalts are comprised at a total concentration of at least 5% by weight, calculated to a total weight of the composition.

4. The composition according to claim 1, wherein the total concentration of the one or more metasilicate salts and the one or more disilicate salts is in the range of 2 to 30% by weight, calculated to a total weight of the composition.

5. The composition according claim 1, wherein the one or more metasilicate salts and the one or more disilicate salts are present at a weight ratio of 10:1 to 1.1:1.

6. The composition according to claim 1, further comprising one or more ammonium salts that are different from the one or more persalts, the one or more metasilicate salts, and the one or more disilicate salts.

7. The composition according to claim 1, further comprising one or more cationic polymers.

8. The composition according to claim 1, further comprising one or more dicarboxylic acids, its salts, or at least one mixture thereof.

9. The composition according to claim 1, further comprising one or more chelating agents.

10. The composition according to claim 1, further comprising one or more thickening polymers.

11. The composition according claim 1, wherein the composition is in the form of a powder, a paste, or a suspension, and further comprises one or more oily lipophilic compounds.

12. The composition according to claim 1, further comprising one or more inert pulverulent carrier materials.

13. The composition according to claim 1, further comprising one or more direct dyes.

14. A method of bleaching hair comprising:

mixing the substantially water free composition according to claim 1 with an aqueous composition to form a mixture, wherein the aqueous composition comprises one or more oxidizing agent and has a pH in the range of 1 to 5, and a weight ratio of the aqueous composition to the substantially water free composition is from 3:1 to 1:3;

applying the mixture onto hair and leaving the mixture on the hair for 5 to 45 minutes; and subsequently rinsing the mixture off from the hair.

15. A kit comprising:

the substantially water free composition according to claim 1; and an aqueous composition comprising one or more oxidizing agents and having a pH in the range of 1 to 5.

* * * * *